(12) United States Patent
Larroque-Lahitette (10) Patent No.: US 9,668,774 B2
(45) Date of Patent: Jun. 6, 2017

(54) BONE FIXING SYSTEM

(71) Applicant: Zimmer Spine, Bordeaux (FR)

(72) Inventor: Gilles Larroque-Lahitette, Lagor (FR)

(73) Assignee: Zimmer Spine, Bourdeaux (FR)

( * ) Notice: Subject to any disclaimer, the term of this patent is extended or adjusted under 35 U.S.C. 154(b) by 76 days.

(21) Appl. No.: 14/695,863

(22) Filed: Apr. 24, 2015

(65) Prior Publication Data

US 2015/0223845 A1    Aug. 13, 2015

Related U.S. Application Data

(63) Continuation of application No. 13/384,180, filed as application No. PCT/EP2010/061085 on Jul. 30, 2010, now Pat. No. 9,039,708.

(30) Foreign Application Priority Data

Jul. 31, 2009    (EP) .................................. 09305720

(51) Int. Cl.
*A61B 17/70* (2006.01)
*A61B 17/82* (2006.01)
*A61B 17/80* (2006.01)
*A61B 17/84* (2006.01)

(52) U.S. Cl.
CPC .......... *A61B 17/7026* (2013.01); *A61B 17/70* (2013.01); *A61B 17/7001* (2013.01); *A61B 17/7032* (2013.01); *A61B 17/7053* (2013.01); *A61B 17/7062* (2013.01); *A61B 17/8028* (2013.01); *A61B 17/82* (2013.01); *A61B 17/842* (2013.01)

(58) Field of Classification Search
CPC . A61B 17/70; A61B 17/7022; A61B 17/7026; A61B 17/842; A61B 17/7053; A61B 17/7032
See application file for complete search history.

(56) References Cited

U.S. PATENT DOCUMENTS

| 2,049,361 A | 7/1936 | Johan |
| 4,570,618 A | 2/1986 | Wu |
| 5,030,220 A | 7/1991 | Howland |
| 5,304,178 A | 4/1994 | Stahurski |

(Continued)

FOREIGN PATENT DOCUMENTS

| EP | 1205152 A1 | 5/2002 |
| EP | 09305720 A1 | 7/2009 |

(Continued)

OTHER PUBLICATIONS

"European Application Serial No. 15174582.5, Extended European Search Report mailed Jun. 1, 2016", 10 pgs.

*Primary Examiner* — Christian Sevilla
(74) *Attorney, Agent, or Firm* — Schwegman Lundberg & Woessner, P.A.

(57) ABSTRACT

This disclosure provides a system for securing a bone to a rod, the system comprising a ligature, a body, and two fasteners. The ligature has two free ends and an intermediate portion therebetween, the intermediate portion being configured to engage a bone. A portion of a rod can be fastened to the body using one of the fasteners. The ligature can be fastened to the body using another one of the fasteners. The two fasteners are distinct from one another and are adapted to fasten two free end portions of the ligature to the body independently from fastening the portion of the rod to the body.

20 Claims, 7 Drawing Sheets

(56) References Cited

U.S. PATENT DOCUMENTS

| | | |
|---|---|---|
| 5,772,663 A | 6/1998 | Whiteside et al. |
| RE36,221 E | 6/1999 | Breard et al. |
| 5,935,133 A | 8/1999 | Wagner et al. |
| 5,964,769 A | 10/1999 | Wagner et al. |
| 6,053,921 A | 4/2000 | Wagner et al. |
| 6,086,590 A | 7/2000 | Margulies et al. |
| 6,179,838 B1 | 1/2001 | Fiz |
| 6,277,120 B1 | 8/2001 | Lawson |
| 6,299,613 B1 | 10/2001 | Ogilvie et al. |
| 6,309,390 B1 | 10/2001 | Le Couedic et al. |
| 6,391,030 B1 | 5/2002 | Wagner et al. |
| 6,514,255 B1 | 2/2003 | Ferree |
| 6,547,790 B2 | 4/2003 | Harkey, III et al. |
| 6,605,091 B1 | 8/2003 | Iwanski |
| 6,682,533 B1 | 1/2004 | Dinsdale et al. |
| 6,695,852 B2 | 2/2004 | Gleason |
| 7,481,828 B2 | 1/2009 | Mazda et al. |
| 7,959,654 B2 | 6/2011 | Mazda et al. |
| 8,128,635 B2 | 3/2012 | Belliard et al. |
| 9,039,708 B2 | 5/2015 | Larroque-Lahitette et al. |
| 2002/0116013 A1 | 8/2002 | Gleason et al. |
| 2009/0138048 A1 | 5/2009 | Baccelli |
| 2009/0182379 A1 | 7/2009 | Baccelli et al. |
| 2009/0248077 A1 | 10/2009 | Johns |
| 2009/0326585 A1 | 12/2009 | Baccelli et al. |
| 2010/0249845 A1 | 9/2010 | Meunier et al. |
| 2011/0034956 A1 | 2/2011 | Mazda et al. |
| 2011/0112581 A1 | 5/2011 | Clement |
| 2011/0238118 A1 | 9/2011 | Baccelli et al. |
| 2011/0238125 A1 | 9/2011 | Baccelli et al. |
| 2012/0022591 A1 | 1/2012 | Baccelli et al. |
| 2012/0022592 A1 | 1/2012 | Belliard |
| 2012/0059377 A1 | 3/2012 | Belliard |
| 2012/0130373 A1 | 5/2012 | Larroque-Lahitette |

FOREIGN PATENT DOCUMENTS

| | | |
|---|---|---|
| WO | 9303681 A1 | 3/1993 |
| WO | 0154599 A1 | 8/2001 |
| WO | 0209604 A1 | 2/2002 |
| WO | 2006106268 A2 | 10/2006 |

BONE FIXING SYSTEM

CROSS-REFERENCE TO RELATED APPLICATIONS

This application is a continuation of U.S. patent application Ser. No. 13/384,180, filed Jan. 13, 2012, which is a U.S. national stage application, which claims the benefit of International Application No. PCT/EP2010/061085, filed Jul. 30, 2010, entitled "BONE FIXING SYSTEM," which claims priority from European Patent Application No. EP 09305720.6, filed Jul. 31, 2009. All applications referenced herein are hereby incorporated by reference in their entireties.

FIELD OF THE INVENTION

The present disclosure relates generally to systems and methods for fixing a bone to a rod. Such systems and methods may be helpful for holding together a bone and a rod in a desired configuration or in a particular relative position. In particular, the bone may be a transverse process or a lamina of a vertebra.

BACKGROUND OF THE INVENTION

One field of application for the invention is fixing bones in a desired position, for example to aid in healing of breaks or in the treatment of scoliosis or otherwise to correct abnormal curvatures of the spine. Other bone deficiencies and abnormalities may also benefit from the invention.

The spine is formed of superposed vertebrae, normally aligned along a vertebral axis, from the lumbar vertebrae to the cervical vertebrae, each having an anterior part, which is the vertebral body, and a posterior part, which is the vertebral arch (or neural arch), the anterior and posterior part enclosing the vertebral foramen. Each vertebral arch is formed by a pair of pedicles and a pair of laminae, and transverse processes and/or a spinous process (or neural spine) project therefrom. The transverse processes and the spinous process project opposite to the vertebral foramen.

When the vertebrae are articulated with each other, the vertebral bodies form a strong pillar for the support of the head and trunk, and the vertebral foramen constitute a canal for the protection of the spinal cord (or medulla spinalis). In between every pair of vertebrae, there are two apertures, the intervertebral foramina, one on either side, for the transmission of the spinal nerves and vessels.

If the spine of a person has abnormal curvature, the vertebrae are typically inclined relative to one another and relative to said vertebral axis. The lateral edges of the vertebrae on one side are therefore closer together and define a concave outline, while the lateral edges on the other side are farther apart and define a convex outline.

In order to straighten the vertebral column as a remedy for this situation, the lateral edges of the vertebrae on the concave side can be moved away from one another and supported at distances from one another substantially equivalent to the distances between the lateral edges on the convex side. To do so, different kinds of devices may be used.

A first kind of device known in the art is a hook and rod system with hooks that are hooked on the internal wall of the vertebral foramen, and rods for connecting two or more hooks together, thereby holding the vertebrae in correct position relative to one another. Known examples of hook and rod system are disclosed, for instance, in the PCT Patent Application No. WO 2005/023126 and in U.S. Pat. No. 4,269,178.

However, using hooks can be difficult because their use increases the risk that the physician (or other operative) might contact and potentially damage the spinal cord that extends along the vertebral foramen (which can result in paralysis of the patient).

Another kind of known device is a screw and rod system with screws that are screwed into the vertebrae, and rods for connecting two or more screws together, thereby holding the vertebrae in correct position relative to one another. A known example of screw and rod system is disclosed, for instance, in the European Patent No. EP 157543381.

The screws typically have tulip-shaped heads and are inserted in pairs into the pedicles on each side of the spinous process on the posterior wall of the vertebrae. The screws therefore constitute fixing points on the vertebrae for holding the vertebrae. However, the screws are inserted into the pedicles of the vertebrae, which in some cases are small or have deteriorated and can be damaged or do not provide sufficient purchase to permanently hold the screw.

Another kind of known device is the system for fixing a bone to a rod, disclosed in WO 2009/047352. It comprises a rod, a blocking body and a conformable elongate member adapted to surround the bone, i.e. to form a loop around it. When using such a system, the elongate member is passed around said bone and through the blocking body and the rod is loaded into the blocking body. The ends of the elongate member are pulled so as to apply tension to the elongate member, and the elongate member and the rod are simultaneously fastened to the blocking body by means of the same fastening system, portion(s) of the elongate member being clamped between the rod and the blocking body. Such a system does not give complete satisfaction because it may be difficult to handle for the physician (or other operative). Indeed, the elongate member and the rod have to be fastened to the blocking body in one single step and, therefore, the elongate member needs to be kept under the desired tension while fastening the rod to the blocking body.

BRIEF SUMMARY OF THE INVENTION

According to one embodiment of the present disclosure, there is provided a bone fixing system for fixing a bone to a rod comprising:

a conformable elongate member having a first free end portion, a second free end portion, and an intermediate portion therebetween;

a main body;

first fastening device or means for fastening a portion of the rod to the main body; and second fastening device or means for fastening the free end portions of the elongate member to the main body, the second fastening device or means being distinct from the first fastening device or means, and the second fastening device or means being suited to operated independently from the first fastening means.

Compared to the bone fixing systems of the prior art, such a bone fixing system is safer and easier to handle. More particularly, since the first and second fastening means are distinct and since the second fastening means may be operated independently from the first fastening means, it is possible to adjust the tension of the elongate member and to fasten the elongate member to the main body, in a first step, and to fasten the rod to the main body in a second step (or vice-versa).

Moreover, the elongate member may be made of a material that presents a certain amount of elasticity so that, even after the physician has pulled and locked in position the free end portions of the elongate member, the elongate member allows a limited amount of relative movement between the bone and the rod while providing a stabilizing effect, thereby providing what is called a dynamic stabilization.

According to an embodiment, the second fastening means comprise a compression member which is movable relative to the main body, the compression member and the main body both defining clamping surfaces between which the free end portions of the elongate member may be inserted, said free end portions being clamped between said clamping surfaces by moving the compression member relative to the main body.

According to an embodiment, the main body is hollow, extends along a first axis from a lower end to an upper end, and comprises:

a main part with upwardly extending side walls defining between them a first internal passage extending along said first axis and opening onto the outside of the main body at its upper end; and a bottom part located under the main part and provided with a second internal passage extending through the entire thickness of the bottom part and communicating with the first internal passage.

In this embodiment, the compression member may be located under said bottom part and be movable relative to said bottom part, the compression member and the bottom part both defining said clamping surfaces, and the bone fixing system may comprise a locking mechanism that passes through the second internal passage and that is to be operated for causing the compression member to move relative to the bottom part.

Thanks to such a conformation, the bone fixing system has a compact design and is easy to handle. Besides, the locking mechanism is accessible and operable through the first internal passage and, therefore, may be operated with a tool being passed through the first internal passage, so as to secure the elongate member to the main body. Thus, the locking mechanism is easily accessible and operable by the physician.

According to an embodiment, the compression member is provided with a threaded hole and said locking mechanism comprises a first screw having a head and a shaft with an external thread, the screw shaft passing through the second internal passage, the screw head bearing on the upper face of the bottom part and having a profile that allows the first screw to be driven, and the external thread of the screw shaft engaging with the threaded hole of the compression member.

According to another embodiment, the second internal passage of the bottom part is provided with an internal thread and the compression member has a protruding part forming said locking mechanism. Said protruding part extends upwardly, has on its upper end a profile that allows the protruding part to be driven, and is provided with an external thread engaging with said internal thread.

According to one embodiment of the present disclosure, there is also provided a method for fixing a bone to a rod, comprising the steps of:

passing a conformable elongate member around said bone and through a bone fixing system according to the present disclosure;

applying tension to the elongate member by pulling on the ends of the elongate member;

fastening the elongate member to the main body by means of said second fastening means;

loading a portion of the rod into the main body;

fastening the rod portion to the main body by means of said first fastening means.

According to the above method, the elongate member may be fastened to the main body before fastening the rod portion to the main body, or vice-versa.

For the physician, the method is easy to use and, more particularly, is effective for holding two or more vertebrae in correct position relative to each other. For so doing, the physician (or other operative) uses at least one bone fixing system and passes the elongate member of the system around a transverse process or a lamina of a vertebra.

Preferably, the physician uses a number of elongate members and bone fixing systems corresponding to the number of vertebrae, with one rod connecting together the bone fixing systems. If the vertebrae need to be held on each side of the spinous processes, it is preferable, to use a number of elongate members and bone fixing systems corresponding to twice the number of vertebrae and two connecting rods (one rod being placed on each side of the spinous processes).

The method has further advantages linked to the use of a bone fixing system according the disclosure.

According to an embodiment, the method uses a bone fixing system according to the disclosure, and comprises the steps of operating the locking mechanism of the system, so as to secure the elongate member to the main body, with a tool which is passed through the first internal passage.

BRIEF DESCRIPTION OF THE DRAWINGS

In the drawings, like reference signs generally refer to the parts throughout the different views. Moreover, parts of different embodiments that have analogous function are identified by the same reference numerals plus 100, 200, etc.

The drawings are not necessarily to scale, emphasis instead generally being placed upon illustrating the principles of the invention.

DETAILED DESCRIPTION OF THE INVENTION

In the following detailed description, it is referred to the accompanying drawings showing several examples of bone fixing systems according to the present disclosure. It is intended that these examples be considered as illustrative but not limiting, the scope of the invention being given by the accompanying claims.

Figure 1:
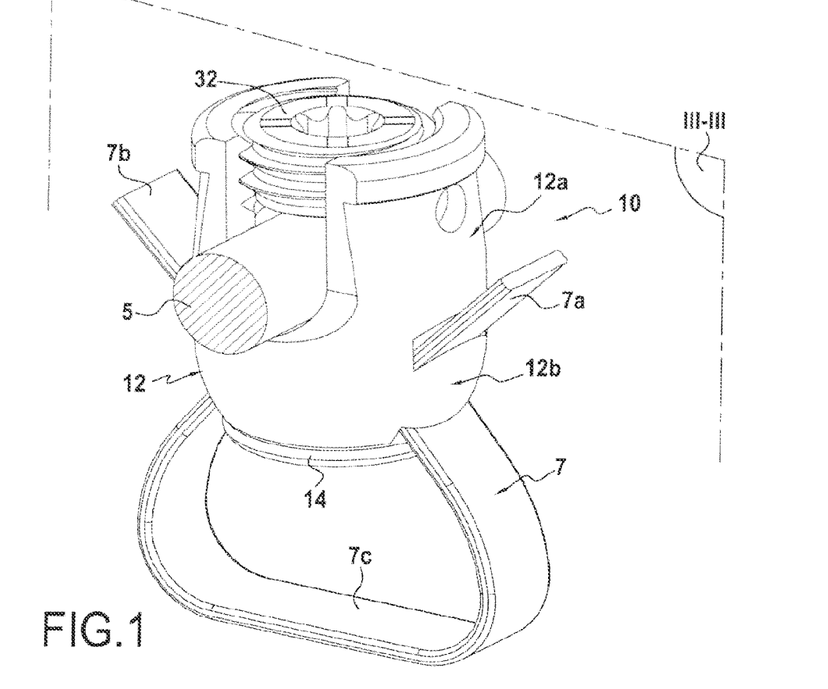
FIG. 1 is a perspective view of an example of bone fixing system according to the present disclosure.
Figure 2:
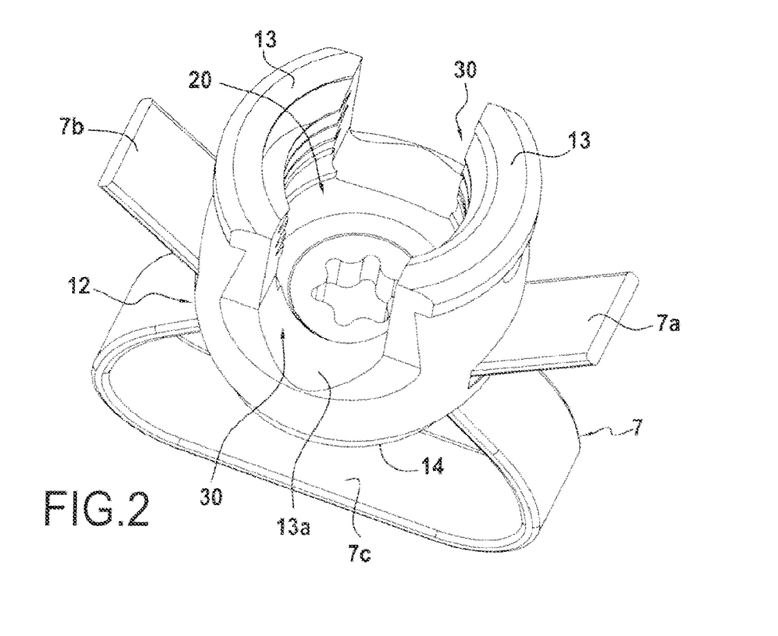
FIG. 2 is a partial perspective view of the bone fixing system of FIG. 1.
Figure 3:
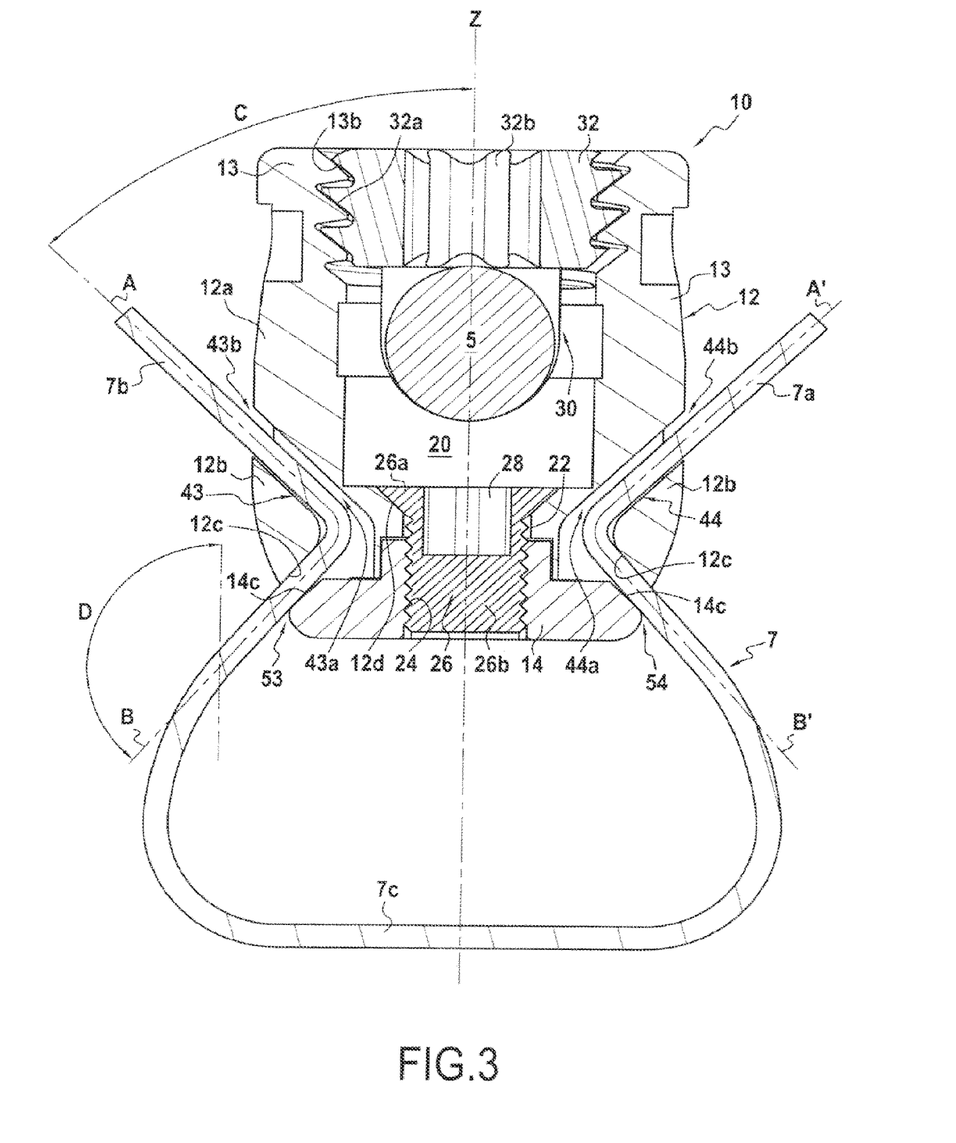
FIG. 3 is a sectional view of the bone fixing system of FIG. 1, along the plane III-III.
Figures 14, 15, 16:
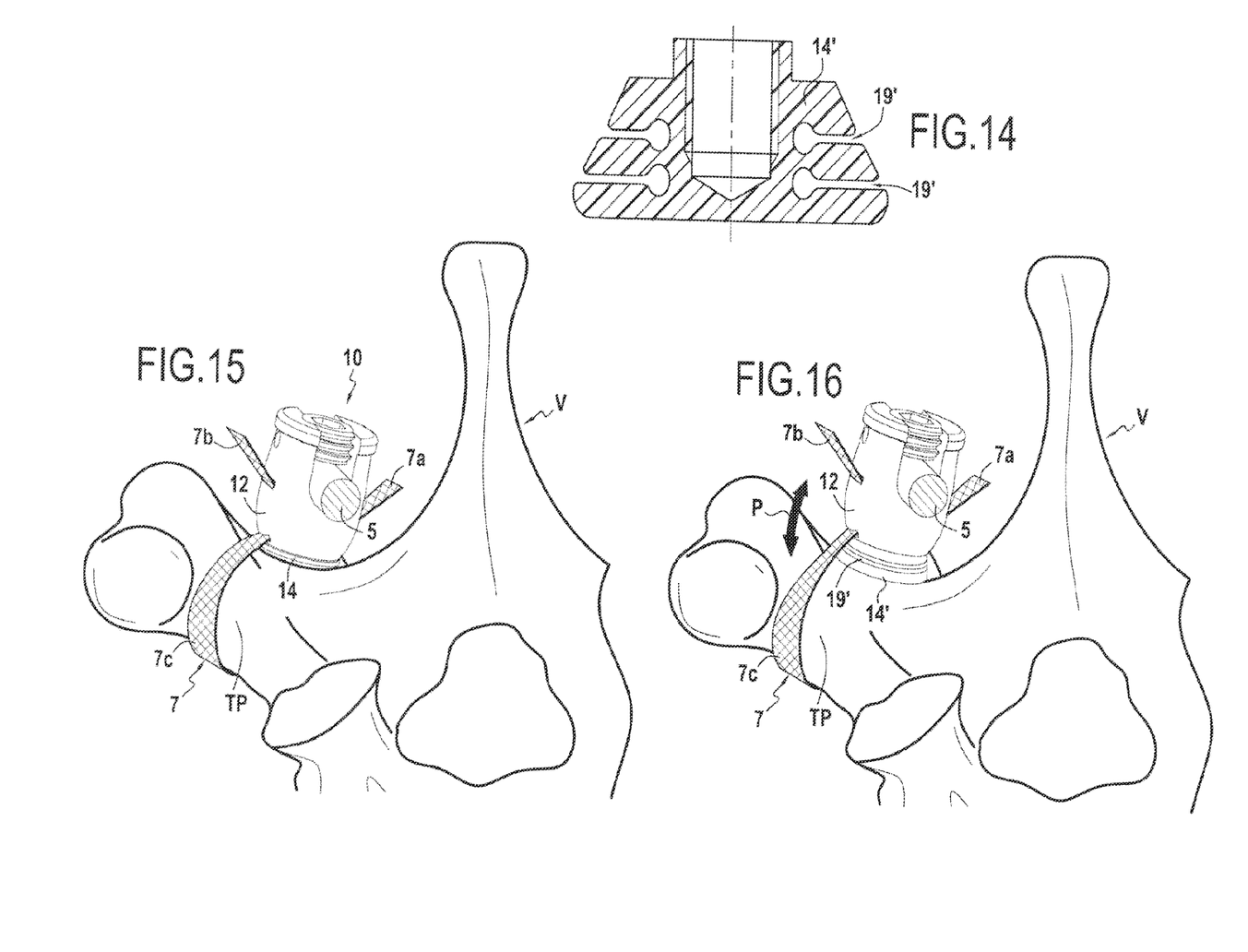
FIG. 14 is a sectional view of another embodiment of the compression member of the bone fixing system.
FIG. 15 is a view showing the bone fixing system of FIG. 1 put into place on a vertebra.
FIG. 16 is a view showing the bone fixing system of FIG. 1 fitted with the compression member of FIG. 14 and put into place on a vertebra.

An example of bone fixing system is shown on FIGS. 1 to 3. The bone fixing system 10 is for fixing a rod 5 (a portion of which is shown in FIGS. 1, 3 and 15) to a bone (see FIG. 15). The bone may be, for instance, a lamina of a vertebra or a transverse process TP of a vertebra V, as shown in FIG. 15.

The bone fixing system 10 comprises a conformable elongate member 7, such as a ligature, having a first free end portion 7a, a second free end portion 7b, and an intermediate portion 7c therebetween, said intermediate portion 7c being adapted to surround the bone (e.g. the transverse process TP);

a main body 12;

first fastening device or means for fastening a portion of the rod 5 to the main body 12; and second fastening device or means for fastening the free end portions 7a, 7b of the elongate member 7 to the main body 12, said second fastening means being distinct from the first fastening means.

The elongate member 7 may be any suitable material that is conformable such as a band, wire, or cord made of metal, a polymeric material, or a combination of the two.

The second fastening means comprise a compression member 14 which is movable relative to the main body 12, the compression member 14 and the main body 12 both defining clamping surfaces 14c, 12c, between which the free end portions 7a, 7b of the elongate member 7 may be inserted, said free end portions 7a, 7b being clamped between said clamping surfaces 12c, 14c by moving the compression member 14 relative to the main body 12.

The main body 12 is hollow, extends along a first axis Z from its lower end to its upper end, and comprises:

a main part 12a with upwardly extending side walls 13 defining between them a first internal passage 20 extending along said first axis Z and opening onto the outside of the main body 12 at its upper end; and a bottom part 12b located under the main part 12a and provided with a second internal passage 22 extending through the entire thickness of the bottom part 12b and communicating with the first internal passage 20.

The main body 12 further comprises third and fourth internal passages 43, 44 through which the first and second free end portions 7a, 7b of the elongate member 7 may be inserted respectively. Each internal passage 43 (44) extends through the main body 12, has two ends 4 43b (44a, 44b) and opens, at one end 43a (44a), in front of the compression member 14 and, at the other end 43b (44b), onto an outer face of the main body and, more precisely, onto a side face of the main body 12. The third and fourth internal passages 43, 44 form guiding means for the free end portions 7a, 7b of the elongate member 7.

In the example the third and fourth internal passages 43, 44 extend, respectively, along third and fourth axis A, A', each of the third and fourth axis forming with respect to said first axis Z an acute angle C which is preferably comprised between 0 and 70.degree. Thus, it is easier for the physician to pull on the ends 7a, 7b of the elongate member 7 for tensioning it.

On the other hand, the clamping surfaces 14c, 12c of the compression member 14 and of the main body 12 define between them fifth and sixth passages 53, 54 extending, respectively, along fifth and sixth axis B, B', each of the fifth and sixth axis forming with respect to said first axis Z an obtuse angle D.

The compression member 14 is provided with a threaded hole 24. Said locking mechanism comprises a first screw 26 having a head 26a and a shaft 26b with an external thread. The screw shaft 26b passes through the second internal passage 22 and the screw head 26a has a profile 28 that allows the first screw 26 to be driven. In the example, the screw head 26a is a socket head and, more particularly, a hex socket head which can be driven, for instance, by an Allen key.

When the first screw 26 is driven, the external thread of the shaft 26b engages with the threaded hole 24 of the compression member 14 and the screw head 26a bears on the upper face 12d of the bottom part 12b. Thus, the clamping surfaces 14c, 12c are brought closer together and the end portions 7a, 7b are locked in position by clamping between the clamping surfaces 14c, 12c.

Turning now to the first fastening means for fastening a portion of the rod 5 to the main body 12, openings 30 are provided in the side walls 13 (see FIG. 2), so that a portion of the rod 5 may be loaded into the main body 12 via said openings 30, and a closure member 32 engages with the main body 12 so as to secure said portion of rod 5 to the main body.

In the example, the main body 12 is provided with a first thread 13b for engagement with a second thread 32a provided on the closure member 32, so that said portion of rod 5 may be clamped between the main body 12 and the closure member by threadably moving the closure member 32 relative to the main body 12. More precisely, in the example, the rod portion is clamped between the edges 13a of the side walls 13 delimiting the bottom of the openings 30, and the lower face of the closure member 32.

In the example, the closure member 32 has an external thread 32a engaging with an internal thread 13b provided on the inner face of the side walls 13. The closure member 32 further comprises a socket head 32b for driving it in rotation.

Figure 4:
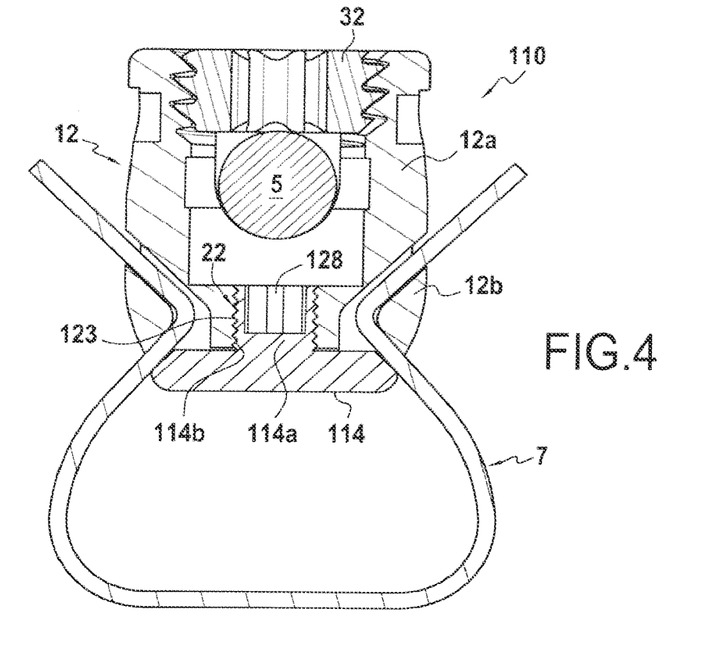
FIG. 4 is a sectional view of another example of bone fixing system according to the present disclosure.

Another example of bone fixing system is shown on FIG. 4. The bone fixing system 110 of FIG. 4 differs from that of FIG. 3 by the locking mechanism. In FIG. 3, the second internal passage 22 of the bottom part 12b is provided with an internal thread 123, and the compression member 114 has a protruding part 114a forming said locking mechanism. Said protruding part 114a extends upwardly, has on its upper end a profile 128 that allows the compression member 114 to be driven in rotation, and is provided with an external thread 114b engaging with said internal thread 123.

It should be noted that, in the examples of FIGS. 1-4, the bottom part 12b of the main body 12 is integral with the main part 12a of the main body 12. This is not the case in the examples of FIGS. 5-7.

Figure 5:
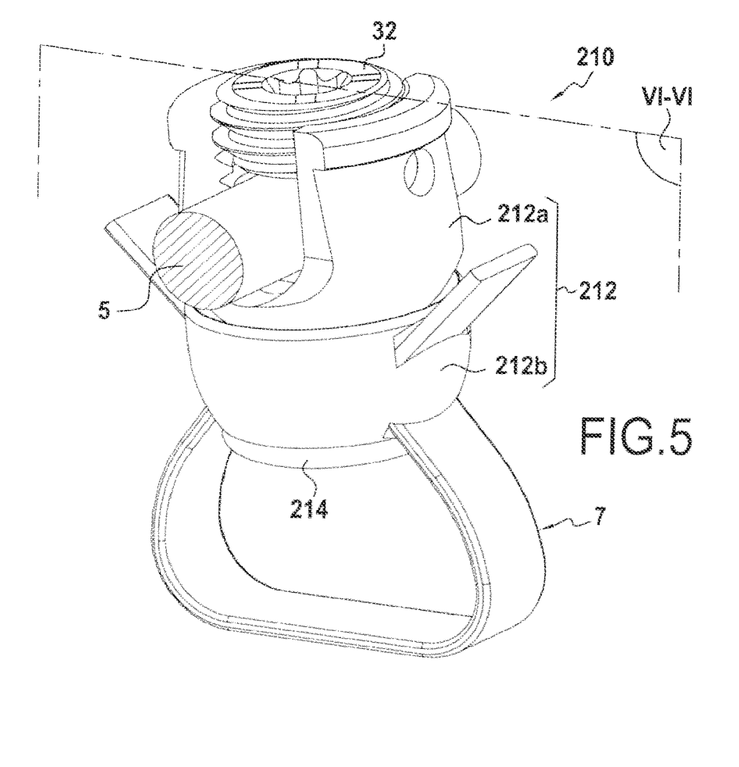
FIG. 5 is a perspective view of another example of bone fixing system according to the present disclosure.
Figure 6:
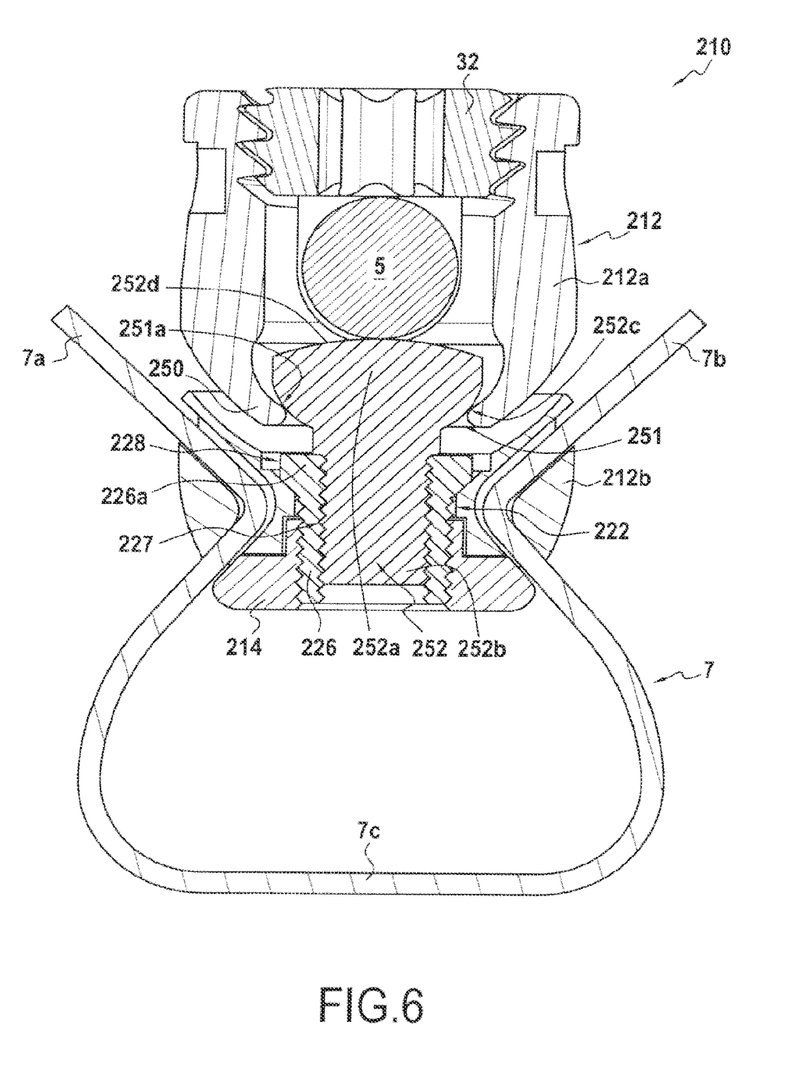
FIG. 6 is a sectional view of the bone fixing system of FIG. 5, along the plane VI-VI.

FIGS. 5 and 6 show another example of bone fixing system 210 differing from that of FIGS. 1-3 in that it comprises a main body 112 with a bottom part 212b and a main part 212a which are not integral with each other.

In this example, the bottom part 212b and the main part 212a of the main body 212 are interconnected by a ball-and-socket connection.

The main part 212a comprises a bottom wall 250, the bottom wall 250 being provided with a through hole 251 delimited by an upper edge 251 a. The ball-and-socket type connection comprises a second screw 252 having a head 252a and a shaft 252b. The screw shaft 252b passes through said through hole 251 and through the second internal passage 222. The screw head 252a has a convex lower face 252c bearing on said upper edge 251a, and a profile that allows the second screw 252 to be driven. For instance, the screw head 252a may be a hex-head or a socket-head. The screw head 252a further has a concave upper face 252d.

When the rod 5 is locked in position by means of the first fastening means, the rod 5 leans against the concave upper face 252d of the second screw 252. More precisely, when the closure member 32 is screwed down, the closure member 32 pushes down on the rod 5 which in turn pushes down on the screw 252 until the convex lower face 252c of the screw head 252a leans against the upper edge 251a of the through hole 251. Since the contact zones between the screw head 252a and the upper edge 251a and between the screw head 252a and the rod 5, are limited, the screw head 252a is able to move with respect to the the main part 212a of the main body 212.

The above structure is one example of a ball-and-socket type connection but other examples could be used.

A ball-and-socket type connection allows a limited amount of relative movement between the bottom part 212b and the main part 212a of the main body 212 and, thus, between the bone and the rod 5, thereby providing or improving the desired dynamic stabilizing effect.

The bottom part 212b is substantially the same as the bottom part 12b of FIG. 3 except for the screw head 226a which has an outer driving profile 228 (instead of the inner driving profile 28), and apart from the fact that the screw 226 is provided with an internal threaded hole 227.

The screw shaft 252b, which has an external thread, passes through the second internal passage 222 and engages with the threaded hole 227, so as to connect together the bottom part 212b and the main part 212a of the main body 212.

Figure 7:
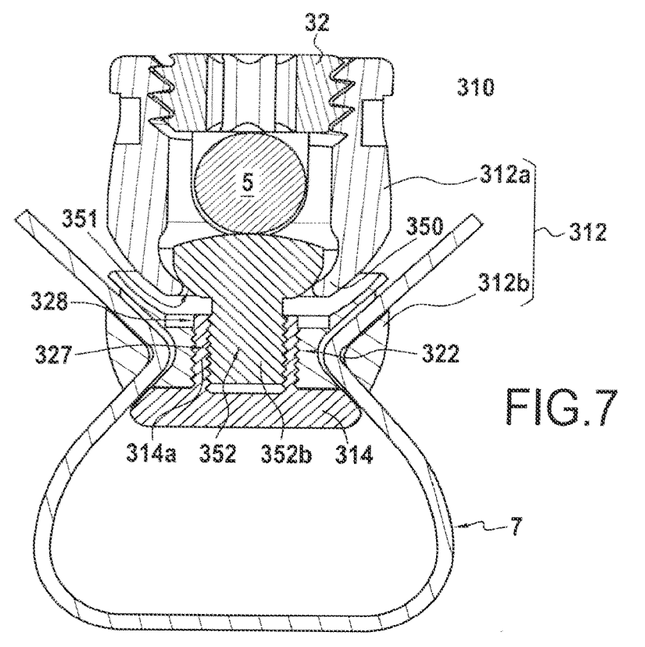
FIG. 7 is a sectional view of another example of bone fixing system according to the present disclosure.

Another example of bone fixing system 310 with a ball-and-socket type connection is shown on FIG. 7. In this example, the main part 312a of the main body 312 and the second screw 352 are the same as those (212a, 252) of FIG. 6, and the bottom part 312b of the main body 312 is substantially the same as the bottom part 12b of FIG. 4 apart from the fact that the protruding part 314a of the compression member 314 has an outer driving profile 328 instead of the inner driving profile 128, and that the compression member 314 is provided with an internal threaded hole 327.

The screw shaft 352b, which has an external thread, passes through the second internal passage 322 and engages with the threaded hole 327, so as to connect together the bottom part 312b and the main part 312a of the main body 312.

In both examples of FIGS. 6 and 7, the screw shaft 252b, 352b passes through the through hole 251, 351 of the bottom wall 250, 350 of the main part 212a, 312a and through the second internal passage 222, 322 and engages with the compression member 214, 314. On FIG. 7, it engages directly with the compression member 314, whereas on FIG. 6, it engages indirectly with the compression member 214, via the screw 226.

Other examples of bone fixing systems 410, 510, 610, 710, for fixing a bone to a rod 5, are shown on FIGS. 8 to 13. Each of them comprises:

a conformable elongate member 7 having a first free end portion 7a, a second free end portion 7b, and an intermediate portion 7c therebetween, said intermediate portion 7c being adapted to surround said bone;

a main body 412, 512, 612, 712;

first fastening device or means for fastening a portion of the rod 5 to the main body 412, 512, 612, 712; and second fastening device or means for fastening the free end portions 7b of the elongate member 7 to the main body 412, 512, 612, 712, said second fastening device or means being distinct from the first fastening device or means.

In the systems of FIGS. 8-12, the first fastening device or means for fastening a portion of the rod 5 to the main body 412, 512, 612, are the same as those of FIG. 1-4 and, therefore, do not need to be described again.

In all the examples of FIGS. 8-13, the second fastening means comprise a compression member which is movable relative to the main body 412, 512, 612, the compression member and the main body both defining clamping surfaces between which the free end portions 7a, 7b of the elongate member 7 may be inserted, said free end portions being clamped between said clamping surfaces by moving the compression member relative to the main body.

Figure 8:
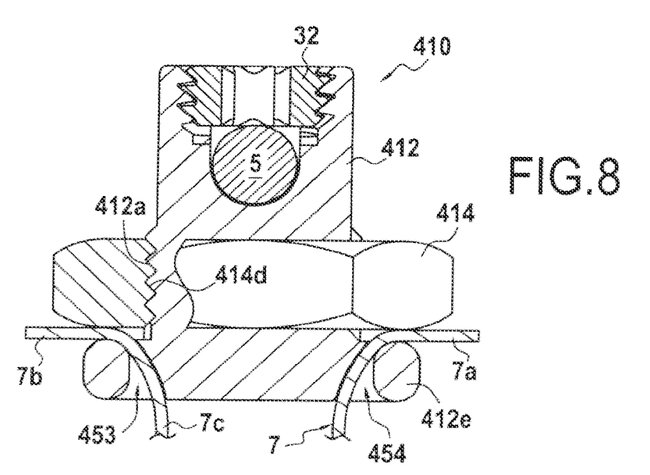
FIG. 8 is a sectional view of another example of bone fixing system according to the present disclosure.

In the example of FIG. 8, the compression member 414 is provided with a thread 414d for rotative engagement with another thread 412a provided on the main body 412, so that the free end portions 7a, 7b of the elongate member 7 may be clamped between a compression part 412e of the main body 412 and the compression member 414 by threadably moving the compression member 414 relative to the main body 412.

In this example, the compression member 414 is a nut provided with an internal thread 414d, and the main body 412 is provided with an external thread 412a. When the compression member 414 is screwed or unscrewed, it moves closer or farther away from the compression part 412e.

The main body 412 comprises:

a compression part 412e which is a flange protruding on the lateral faces of the main body 412, and two internal passages 453, 454 through which the first and second free end portions 7a, 7b of the elongate member may be inserted respectively, each of the third and fourth internal passages 453, 454 extending through the main body, having two ends and opening, at one end, in front of the compression member 414 and, at the other end, onto an outer face of the main body 412 and, more precisely, onto the end face of the main body 412 which is opposite to the other end face receiving the rod 5.

When the compression member 414 is threadably engaged with the main body 412, it moves closer or farther away from the compression part 412e.

Figure 9:
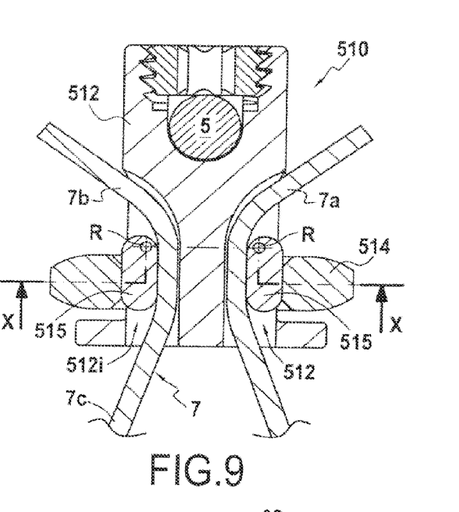
FIG. 9 is a sectional view of another example of bone fixing system according to the present disclosure.
Figure 10:
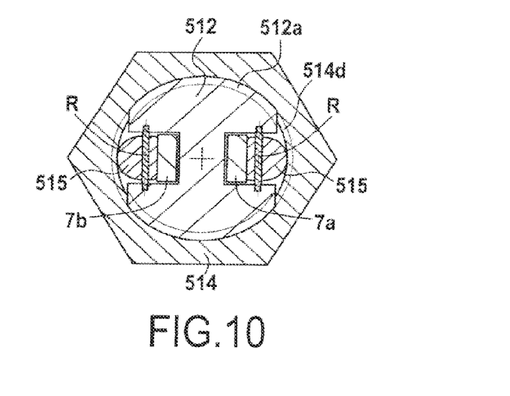
FIG. 10 is a sectional view of the bone fixing system of FIG. 9, along the plane X-X.

In the example of FIG. 9, the compression member 514 is also a nut provided with an internal thread 514d (see FIG. 10), and the main body 512 is also provided with an external thread 512a, but in this case, the compression member 514 is not in direct contact with the elongate member 7. Indeed, the compression member 514 cooperates with two profiled rotating pieces 515 which are rotatably mounted (around the axis R) in recesses 512i provided on the lateral faces of the main body 512. When the compression member 514 moves along the main body 512, it pushes the rotating pieces 515 in the recesses 512i, and each free end portion 7a, 7b of the elongate member is clamped between a rotating piece 515 and the bottom wall of the recess 512i.

Figure 11:
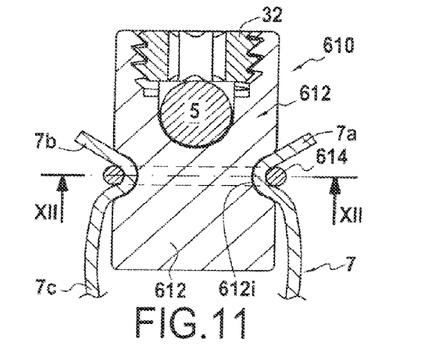
FIG. 11 is a sectional view of another example of bone fixing system according to the present disclosure.
Figure 12:
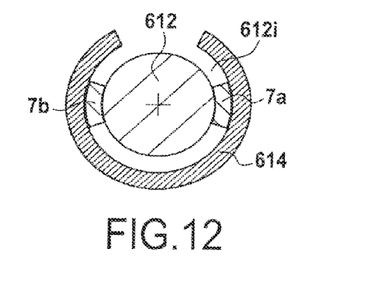
FIG. 12 is a sectional view of the one fixing system of FIG. 11, along the plane XII-XII.

In the example of FIG. 11, the compression member 614 is a circlip and the main body has a peripheral groove 612i for receiving the free end portions 7a, 7b of the elongate member and the compression member 614. The free end portions 7a, 7b are inserted and clamped between the bottom of the groove 612i and the compression member 614.

The compression member 614 could also be a fastening collar.

The peripheral groove 612i may extend along the entire circumference of the main body 612, or along a part of it.

Figure 13:
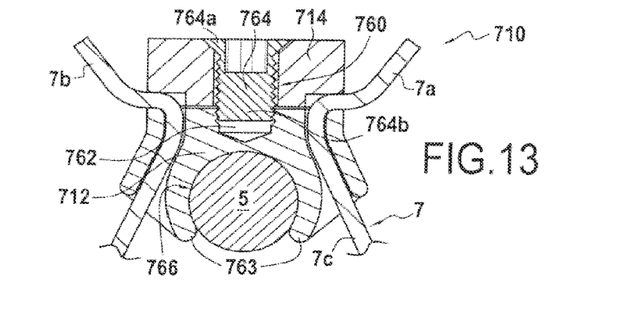
FIG. 13 is a sectional view of another example of bone fixing system according to the present disclosure.

In the example of FIG. 13, the second fastening device or means comprise a screw 764 and a compression member 714 which is provided with a through hole 760. The main body 712 of the bone fixing system 710 is provided with a threaded hole 762 aligned with said through hole 760. The shaft 764b of the screw 764 passes through said through hole 760 and is threadably engaged with the threaded hole 762. The head 764a of the screw 764 is intended to lean against the upper surface of the compression member 714. The compression member 714 and the main body 712 both define clamping surfaces between which the free end portions 7a, 7b of the elongate member may be inserted and clamped, said free end portions being clamped by screwing the screw 764 into the main body 712.

In the example of FIG. 13, the first fastening device or means comprise a seat part 766 for receiving a portion of the rod 5, the seat part 766 facing the intermediate portion 7c of the elongate member 7, said portion of rod 5 being clamped between the seat part 766 and the intermediate portion 7c of the elongate member by tightening the elongate member 7 (i.e. by pulling on the free end portions 7a, 7b of the elongate member 7). Preferably, the seat part 766 is a clip for holding the rod 5. For instance, the seat part 766 is delimited by two open arms 763 with certain elasticity, said arms 763 partially surrounding the rod 5.

Turning now to FIG. 15, the bone fixing system 10 of FIGS. 1-3 is shown in a tightened position around a vertebra V. More precisely, the intermediate portion 7c of the elongate member 7 surrounds the transverse process TP of the vertebra.

By pulling on the ends of the elongate member 7, the compression member 14 of the system 10 comes into contact with the transverse process TP.

The compression member 14 may be made In a soft material, order to avoid damaging the vertebra V and/or to allow a limited amount of relative movement between the vertebra V and the system 10, and thus between the vertebra V and the rod 5, thereby providing a dynamic stabilization effect, More particularly, compared to the material which makes up the main body 12 and which is preferably rigid, the material the compression member 14 is softer.

In order to improve the cushioning effect and/or the dynamic stabilization effect, the compression member 14' may be provided with at least one peripheral groove 19' on its side faces. Such a peripheral groove 19' makes the deformation of the compression member 14' easier and allows the member 14' to bend laterally and to compress axially. Thus a limited amount of relative movement (including pivoting movement) between the vertebra V and the system 10 is allowed, as illustrated by the double arrow P on FIG. 16.

The invention claimed is:

1. A system for securing a bone to a rod, comprising:
a conformable elongate member having a first free end portion, a second free end portion, and an intermediate portion extending therebetween, the intermediate portion being configured to engage a bone;
a main body having a first opening for receiving the first free end portion, a second opening for receiving the second free end portion, and a passageway extending through the main body transverse to the first opening and the second opening, the passageway being configured to receive a rod therein;
a first threaded fastener configured to secure the first free end portion and the second free end portion to the main body; and
a second threaded fastener configured to secure the rod within the passageway.

2. The system of claim 1, wherein the first opening and the second opening are spaced apart from each other on an exterior of the main body.

3. The system of claim 1, wherein the first opening and the second opening are independent of each other.

4. The system of claim 1, wherein the first threaded fastener is configured to be received within a first aperture of the main body and the second threaded fastener is configured to be received within a second aperture of the main body.

5. The system of claim 1, wherein the rod is securable within the passageway with the second threaded fastener independently of securing the first free end portion and the second free end portion to the main body with the first threaded fastener.

6. A system for securing a bone to a rod, comprising:
a conformable elongate ligature having a first free end portion, a second free end portion, and an intermediate portion therebetween, the intermediate portion being configured to engage a bone;
a main body having a first passageway extending therethrough, a second passageway extending therethrough, and a third passageway extending therethrough;
wherein the third passageway is independent of the first passageway and the second passageway, the third passageway being configured to receive a portion of a rod therein, the first passageway being configured to receive the first free end portion therein, and the second passageway being configured to receive the second free end portion therein;
a first threaded fastener configured to secure the first free end portion and the second free end portion to the main body; and
a second threaded fastener configured to secure the portion of the rod to the main body.

7. The system of claim 6, wherein the intermediate portion of the conformable ligature is configured to extend from the main body in a direction transverse to a longitudinal axis of the rod.

8. The system of claim 6, wherein the main body is configured to maintain the first threaded fastener spaced apart from the second threaded fastener.

9. The system of claim 6, wherein the first threaded fastener is configured to secure the first free end portion and the second free end portion to the main body independently of the second threaded fastener securing the portion of the rod to the main body.

10. The system of claim 6, wherein the second threaded fastener includes external threads configured to engage internal threads formed within the main body.

11. The system of claim 6, wherein the first passageway opens to an exterior surface of the main body at a first location, and the second passageway opens to the exterior surface of the main body at a second location different from the first location.

12. The system of claim 11, wherein the intermediate portion is extendable between the first and second locations exterior of the main body.

13. A system for securing a bone to a rod, comprising:
   a flattened conformable elongate ligature having a first free end portion, a second free end portion, and an intermediate portion therebetween, the intermediate portion being configured to engage a bone;
   a main body having a first opening in a lower surface for receiving the first free end portion, a second opening in the lower surface for receiving the second free end portion, and a passageway extending through the main body transverse to the first opening and the second opening, the passageway being configured to receive a portion of a rod therein;
   a first fastener configured to secure the first free end portion and the second free end portion to the main body; and
   a second fastener configured to secure the portion of the rod to the main body within the passageway.

14. The system of claim 13, wherein the intermediate portion is configured to form a loop extending away from the main body, the loop being adapted to surround the bone.

15. The system of claim 14, wherein the loop is extendable between the first and second openings exterior of the main body.

16. The system of claim 13, wherein the first fastener is configured to secure the first free end portion and the second free end portion independently of the second fastener securing the portion of the rod.

17. The system of claim 13, wherein the first opening and the second opening are spaced apart from each other in the lower surface of the main body.

18. The system of claim 13, wherein the first fastener and the second fastener are maintained in a spaced apart relationship by the main body.

19. The system of claim 13, wherein the flattened conformable elongate ligature has a width, a length, and a thickness, the width being greater than the thickness and the length being greater than the width.

20. The system of claim 13, wherein the main body is devoid of external threading.

\* \* \* \* \*

UNITED STATES PATENT AND TRADEMARK OFFICE
CERTIFICATE OF CORRECTION

PATENT NO. : 9,668,774 B2  
APPLICATION NO. : 14/695863  
DATED : June 6, 2017  
INVENTOR(S) : Gilles Larroque-Lahitette Page 1 of 1

It is certified that error appears in the above-identified patent and that said Letters Patent is hereby corrected as shown below:

On the Title Page

In item (73), in "Assignee", in Column 1, Line 1, delete "Bourdeaux" and insert --Bordeaux-- therefor In item (30), in "Foreign Application Priority Data", in Column 1, Line 1, delete "09305720" and insert --09305720.6-- therefor Signed and Sealed this  
Tenth Day of July, 2018

Andrei Iancu  
*Director of the United States Patent and Trademark Office*